(12) United States Patent
Ishii et al.

(10) Patent No.: US 8,944,679 B2
(45) Date of Patent: Feb. 3, 2015

(54) ELECTRODE MEMBER, ELECTRON ENERGY ANALYZER, PHOTOELECTRON ENERGY ANALYZER, AND TEMPERATURE MEASURING APPARATUS

(75) Inventors: Juntaro Ishii, Tsuchiura (JP); Ikuo Kinoshita, Yokohama (JP)

(73) Assignees: National Institute of Advanced Industrial Science and Technology (JP); Public University Corporation Yokohama City University (JP)

( * ) Notice: Subject to any disclaimer, the term of this patent is extended or adjusted under 35 U.S.C. 154(b) by 28 days.

(21) Appl. No.: 13/392,569

(22) PCT Filed: Aug. 18, 2010

(86) PCT No.: PCT/JP2010/063894
§ 371 (c)(1),
(2), (4) Date: Feb. 27, 2012

(87) PCT Pub. No.: WO2011/024677
PCT Pub. Date: Mar. 3, 2011

(65) Prior Publication Data
US 2012/0155509 A1    Jun. 21, 2012

(30) Foreign Application Priority Data

Aug. 28, 2009 (JP) ............................... P2009-197670

(51) Int. Cl.
*G01K 11/00* (2006.01)
*G21K 1/08* (2006.01)
(Continued)

(52) U.S. Cl.
CPC .............. *G01N 23/227* (2013.01); *G01K 11/30* (2013.01)
USPC ............... 374/159; 374/E11.001; 250/396 R; 250/381

(58) Field of Classification Search
CPC .......... H01J 49/067; H01J 37/05; G21K 5/04; G01R 31/305; G01T 1/29

USPC .......... 379/159; 374/E11.001, 161, E11.015, 374/159
See application file for complete search history.

(56) References Cited

U.S. PATENT DOCUMENTS 3,749,926 A * 7/1973 Lee ............................... 250/305
4,758,723 A * 7/1988 Wardell et al. ................ 250/305
(Continued)

FOREIGN PATENT DOCUMENTS

JP      57-072072      5/1982
JP      6-003295       1/1994
(Continued)

OTHER PUBLICATIONS

International Search Report mailed Oct. 5, 2010 in corresponding PCT International Application No. PCT/JP2010/063894.
(Continued)

*Primary Examiner* — Lisa Caputo
*Assistant Examiner* — Nasir U Ahmed
(74) *Attorney, Agent, or Firm* — Ostrolenk Faber LLP

(57) ABSTRACT

An electrode member has a plurality of spherical electrode sections wherein the radiuses of the spherical sections are different from each other. The spherical electrode sections are disposed in a state wherein the center points of the respective spheres match each other and the spherical electrode sections are insulated from each other such that voltages can be independently applied thereto. Electron-passing openings for electrons, which move from the center point to the outside of the electrode member, are formed at positions where the spherical electrode sections and a plurality of straight lines radially extending from the center point intersect each other.

6 Claims, 7 Drawing Sheets

(51) Int. Cl.
*G01N 23/227* (2006.01)
*G01K 11/30* (2006.01)

(56) References Cited

U.S. PATENT DOCUMENTS

| | | | |
|---|---|---|---|
| 5,442,183 A * | 8/1995 | Matsui et al. | 250/441.11 |
| 6,787,772 B2 * | 9/2004 | Ose et al. | 850/9 |
| 7,238,941 B2 * | 7/2007 | Tai et al. | 250/338.1 |
| 7,331,709 B2 * | 2/2008 | Bando et al. | 374/201 |
| 7,718,961 B1 * | 5/2010 | Browning | 250/306 |
| 2006/0007983 A1 * | 1/2006 | Tai et al. | 374/121 |
| 2006/0222047 A1 * | 10/2006 | Reading | 374/120 |
| 2009/0200463 A1 * | 8/2009 | Degenhardt et al. | 250/307 |
| 2010/0131226 A1 * | 5/2010 | Takizawa | 702/130 |

FOREIGN PATENT DOCUMENTS

| | | |
|---|---|---|
| JP | 10-188883 | 7/1998 |
| JP | 2009-123850 | 6/2009 |

OTHER PUBLICATIONS

Written Opinion mailed Oct. 5, 2010 in corresponding PCT International Application No. PCT/JP2010/063894.

Chemical Society of Japan, Chemical Reviews, No. 16, Electron Spectroscopy, Academic Press Center, Jul. 10, 1977, pp. 20-25, with partial English translation thereof.

* cited by examiner

US 8,944,679 B2

ELECTRODE MEMBER, ELECTRON ENERGY ANALYZER, PHOTOELECTRON ENERGY ANALYZER, AND TEMPERATURE MEASURING APPARATUS

CROSS-REFERENCE TO RELATED APPLICATIONS

The present application is a 35 U.S.C. §§371 national phase conversion of PCT/JP2010/063894, filed Aug. 18, 2010, which claims priority of Japanese Patent Application No. 2009-197670, filed Aug. 28, 2009, the contents of which are incorporated herein by reference. The PCT International Application was published in the Japanese language.

TECHNICAL FIELD

The present invention relates to an electrode member, an electron energy analyzer, a photoelectron energy analyzer, and a temperature measuring apparatus, and more particularly, to an electron measuring technique in which highly sensitive measurement is possible, high energy resolution is realized, an absolute temperature (a thermodynamic temperature) at a surface of a material such as a metal can be measured with high precision, a use as a standard thermometer for a surface temperature is possible, and a small size and a low price are realized.

BACKGROUND ART

In related art, methods to measure sample temperature may be classified as a contact method, which typically employs a thermocouple or a resistance thermometer, or as a non-contact method, which typically employs an infrared radiation thermometer.

Since the contact method enables a configuration of an apparatus to be simple and inexpensive and a temperature of a sample to be directly measured, the contact method is widely used in various fields. However, the contact method is not an effective temperature measurement means with respect to a clean surface, a surface of a thin film in a thin film manufacturing process, or a sample of dimensions on the order of nanometers, since a sensor part of the thermocouple or the resistance thermometer is large and thermally contacts a measurement object.

In recent times, while local temperature measurement for Scanning Thermal Microscopy (SThM) has been attempted by installing a thermocouple or a resistance thermometer at an end of an Atomic Force Microscope (AFM) tip, definition of a measured physical value is unclear and simultaneous multi-functional measurement with another surface analysis measurement is impossible because of the required complexity of the measuring apparatus.

In addition, the infrared radiation thermometer, which is being widely distributed as a practical thermometer, measures thermal radiation from a surface of a material and determines the temperature of the material from a wavelength distribution or intensity of the thermal radiation. However, since an actual material is not an ideal blackbody radiation source, a thermal radiation amount from the surface of the material depends on thermo-optical properties (emissivity) of the surface. Accordingly, if there is no detailed information on the emissivity of the material, the surface temperature of the measurement object cannot be precisely measured.

As described above, due to the above-mentioned reasons, there is no practical temperature measuring means that can satisfy the following measurement needs in surface analysis or nano-scientific measurement fields: (a) locality (surface selectivity), (b) non-contact and (c) simultaneous multi-functional measurement.

Meanwhile, in the related art, it is well known that an energy distribution of electronic states of a material such as a metal is represented as a function of temperature by a Fermi distribution function, and such Fermi distribution is measured, so that the temperature of the material can be directly determined.

The Fermi distribution function is a probability distribution function of electrons depending on an absolute temperature T as represented by the following equation (1)

[Equation 1]

$$f(E, T) = \frac{1}{\exp\left(\frac{E - E_F}{k_B T}\right) + 1} \quad (1)$$

In the above equation (1), $E_F$ represents Fermi energy, $k_B$ represents the Boltzmann constant, and the function $f(E,T)$ represents probability of electron occupancy in states at energy E.

Since the Fermi distribution function depends on only an absolute temperature T, when a Fermi distribution curve in a certain material can be obtained, the absolute temperature T of the material can be unambiguously determined from the Fermi distribution curve. When a technique of measuring a Fermi distribution of electrons with high resolution and determining a temperature of a material from the Fermi distribution function is developed, temperature measurement that satisfies the above conditions (a) to (c) becomes possible.

In the related art, measurement of electron energy states of a material may contains include such methods as scanning tunneling microscopy (STM), ultraviolet photoelectron spectroscopy (UPS), X-ray photoelectron spectroscopy (XPS), or Auger electron spectroscopy (AES).

While STM is appropriate for measuring local density of states, intensity of tunnel current that can be obtained through the measurement is overlap integral between electronic states of a sample and a metal tip, and Fermi distribution of electrons in the sample cannot be directly measured.

Meanwhile, UPS or XPS uses an apparatus for applying irradiating light in an ultraviolet or x-ray region to a sample and measuring the kinetic energy of excited electrons emitted from the sample. A high energy edge of such an electron spectrum is due to photoelectron emission from a state at Fermi energy ($E_F$) of the sample, and the shape of the high energy edge of the photoelectron spectrum reflects the Fermi distribution of the sample.

In addition, XPS or AES employs an excitation source of several keV, which is appropriate to chemical analysis measuring an inner shell electron. Further, in order to measure electronic states of a valence band around the Fermi energy with high energy resolution, UPS is optimal. Further, in UPS, since an escape depth of the electrons excited by light in an ultraviolet region or a vacuum ultraviolet region is several angstroms, information on the electronic states in several atomic layers on the surface can be obtained.

Conventional electron energy analyzers used in electron spectroscopy (UPS, XPS, or AES) may be categorized as a retarding electric field type or as an electrostatic deflection type. The retarding electric field type uses a method of analyzing electron energy by passing only electrons with kinetic energy higher than potential of the retarding electrodes (barrier potential) and preventing electrons with lower energy from passing, which is conventionally used to measure electrons with relatively high energy of several keV with no necessity for high energy resolution. The electrostatic deflection type is used to measure the energy of electrons smaller than several keV with high energy resolution.

In particular, in measurement by UPS for material investigations, angle-resolved measurement of electrons emitted from a sample is important, and mainly a concentric electrostatic hemispherical analyzer with an angular resolution is used, Chemical Society of Japan, Chemical Reviews, No. 16, Electron Spectroscopy, Academic Press Center, Published on Jul. 10, 1977, pages 20 to 25.

Meanwhile, in AES, a hemispherical retarding type analyzer is often used. Since the hemispherical retarding type analyzer detects electrons in a wide detection angle (a solid angle), in comparison with a concentric electrostatic hemispherical analyzer, in general, measurement with high sensitivity is possible with a hemispherical retarding type analyzer.

SUMMARY OF INVENTION

Problems to be Solved by the Invention (1) Necessity for Electron Energy Analyzer Having High Sensitivity and High Energy Resolution In order to determine practically a temperature from a measured photoelectron spectrum, Fermi distribution measurement with high sensitivity and high energy resolution is needed. With regard to the high sensitivity, in order to determine a temperature value by fitting a Fermi distribution function to a photoelectron spectrum, it is necessary to measure the photoelectron spectrum at a high S/N ratio. In addition, with regard to the high energy resolution, when practical temperature resolution of a 1° C. level is realized as temperature measurement, the energy resolution required for Fermi distribution measurement is about 3 meV or less.

Further, for practical temperature measurement in surface analysis, for example, it is useful to perform simultaneous measurement with various measuring apparatuses such as a probe for electrical property measurement. It is necessary for a surface analysis apparatus available in the market to be able to be mounted on one sensor port of a vacuum chamber as a temperature measuring apparatus. For this reason, a compact and inexpensive electron energy analyzer is needed.

(2) Affairs of Conventional Concentric Electrostatic Hemispherical Analyzer

While the conventional concentric hemispherical electrostatic analyzer has good angular resolution, since a detection angle of electrons is small, the concentric hemispherical electrostatic analyzer has lower measurement sensitivity than the retarding electric field analyzer. In addition, the energy resolution is about 10 meV, which is insufficient to perform practical temperature measurement.

Further, while the concentric hemispherical analyzer available in the market includes an apparatus having energy resolution of about 3 meV, since the energy resolution of the apparatus depends on a radius of a hemispherical electron path, the apparatus is very huge and is very expensive. Hence, the apparatus is not practical for temperature measuring.

(3) Affairs of Conventional Retarding Electric Field Electron Energy Analyzer

The conventional hemispherical retarding type analyzer uses a hemispherical grid formed of a metal mesh as an electrode (a metal mesh electrode), and electrons move in an electrostatic field formed by the metal mesh electrodes. Here, electrons having relatively high kinetic energy move along a straight line radially extending from a sample surface to perpendicularly enter a retarding electrode. However, since electrons having relatively low kinetic energy have a curved flight trajectory due to a force from a locally non-uniform electrostatic field formed by the metal mesh electrode, the electrons cannot perpendicularly enter the retarding electrode, and electron energy may be measured at an underrated value.

In addition, since hemispherical potential formed by the metal mesh electrode is spatially non-uniform, electrons having different flight trajectories move on different barrier potentials. Accordingly, electron energy measured by the hemispherical retarding type analyzer is generally limited to about 100 eV or more, and it is difficult to measure electrons having lower kinetic energy than about 100 eV.

Further, since energy resolution of measurement for electrons having energy of about 100 eV is about 0.1 eV, the conventional hemispherical retarding type analyzer cannot be applied to practical temperature measurement.

In order to solve the problems above, the present invention is directed to an electrode member, an electron energy analyzer, a photoelectron energy analyzer, and a temperature measuring apparatus that enable high sensitivity measurement, provide high energy resolution, measure an absolute temperature (a thermodynamic temperature) at a surface of a material such as a metal with high precision, and enable use as a standard surface temperature thermometer with a compact size and a low price.

Means for Solving the Problems

An electrode member in accordance with the present invention may include: a plurality of spherical electrode parts, each of the plurality of spherical electrode parts having a radius, the radii being different from each other, and wherein the spherical electrode parts are disposed in an insulated state such that spherical center points thereof coincide with one another and voltages are independently applied to the spherical electrode parts, and electron passage openings, configured to extract electrons moving from the center point to an outside of an electrode, are respectively formed at positions of the spherical electrode parts crossing a plurality of straight lines radially extending from the center point.

An electron energy analyzer in accordance with the present invention may have the electrode member described above.

The electron energy analyzer in accordance with the present invention may have an electron detection part configured to detect a position of an electron that reaches a detection unit so as to identify the direction in which an electron passes through the electrode part, the electron detection part being disposed behind the spherical electrode part.

In the photoelectron energy analyzer in accordance with the present invention, the electron energy analyzer described above may have an excitation light source configured to irradiate a sample to cause the sample to emit photoelectrons from a surface of the sample disposed at a spherical center point of the spherical electrode part, wherein the spherical electrode part detects the photoelectrons emitted from the surface of the sample disposed at the spherical center point.

Preferably, in the photoelectron energy analyzer in accordance with the present invention, the excitation light source may have a guide part configured to guide light irradiated from the excitation light source to the spherical center point of the spherical electrode part.

A temperature measuring apparatus in accordance with the present invention may have the photoelectron energy analyzer described above.

Effect of the Invention

The electrode member according to the present invention has a plurality of spherical electrode parts having different radii, so that the spherical electrode parts have the same spherical center point. In addition, the spherical electrode parts are arranged to be insulated from each other to independently apply voltages. Since electron passage openings are formed at positions crossing a plurality of straight lines of the spherical electrode parts radially extending from the center point to extract the electrons moving from the center point to the outside of the electrode in a straight line, appropriate voltages are applied to the spherical electrode parts so that electrostatic lenses for the electrons may be formed between the adjacent electrode parts.

In addition, the electrons emitted from the sample fly freely to pass through the opening of the innermost spherical electrode part, a flight trajectory of the electrons is controlled by the electrostatic lens, and finally, the electrons perpendicularly enter a center portion of the opening of the outermost spherical electrode part (retarding electrode). While the electrons having higher kinetic energy than the barrier potential formed at the outermost spherical electrode part can pass through the outermost spherical electrode part, the electrons having lower kinetic energy than the barrier potential cannot pass through the outermost spherical electrode part. Accordingly, only the electrons passing through the outermost spherical electrode part are counted by a detection part. Such electron intensity is recorded while scanning the retarding voltage applied to the outermost spherical electrode part, and thus, an integrated electron energy spectrum can be obtained. Further, as the obtained integrated electron energy spectrum is subjected to differential calculation, for example, in a computer, a desired electron spectrum can be obtained.

In addition, since the retarding electric field type is employed and the electrode member has a spherical shape, the photoelectrons emitted from the sample are detected within a range of a large solid angle, a maximum of $2\pi$, and high sensitivity measurement can be realized in comparison with the conventional concentric hemispherical electrostatic analyzer.

Further, a voltage is applied to each of the spherical electrode parts so that an electrostatic lens is configured between the openings of adjacent spherical electrode parts, controlling a trajectory of the photoelectrons emitted from the sample. Accordingly, the electrons entering the outermost spherical electrode part (retarding electrode) can converge at a center portion in which potential of the opening is uniform, and the electrons can perpendicularly enter the outermost spherical electrode part (retarding electrode). Therefore, high energy resolution not available in the related art can be realized.

Further, as an electron detector that can determine a position of electrons on the detector arriving at the detection part is used, the number of electrons can be counted at each emission angle of the electrons emitted from the sample. Accordingly, electron energy spectra of emission angles of the photoelectrons to a wide emission angle range can be simultaneously measured using the electron energy analyzer of the present invention, without scanning installation positions of the electron energy analyzer with respect to the samples.

According to the electron energy analyzer of the present invention, since the electrode member of the present invention is provided, a compact and inexpensive analyzer can be realized.

According to the photoelectron energy analyzer of the present invention, since the electron energy analyzer of the present invention further includes an excitation source for emitting photoelectrons from a surface of a sample disposed at a spherical center point of the spherical electrode part, a compact and inexpensive photoelectron energy analyzer in comparison with the conventional concentric hemispherical analyzer having high energy resolution can be realized.

As described above, it is possible to realize an electron energy analyzer and a photoelectron energy analyzer, which are compact, inexpensive and easily practicable, having high sensitivity and high energy resolution not available in the related art. Accordingly, an absolute temperature (thermodynamic temperature), for example, of a surface of a metal, for example, can be practically measured.

Since the temperature measuring apparatus of the present invention is constituted by the photoelectron energy analyzer of the present invention, there is no necessity for temperature scale calibration by a temperature fixed point, for example. Accordingly, the temperature measuring apparatus can be used as a standard thermometer, which does not require a temperature scale calibration against a reference temperature standard.

BEST MODE FOR CARRYING OUT THE INVENTION

Hereinafter, embodiments for implementing an electrode member, an electron energy analyzer, a photoelectron energy analyzer, and a temperature measuring apparatus in accordance with the present invention will be described.

In addition, the embodiment is specifically described so that the spirit of the present invention is better understood, but does not limit the invention unless the context clearly indicates otherwise.

Figure 1:
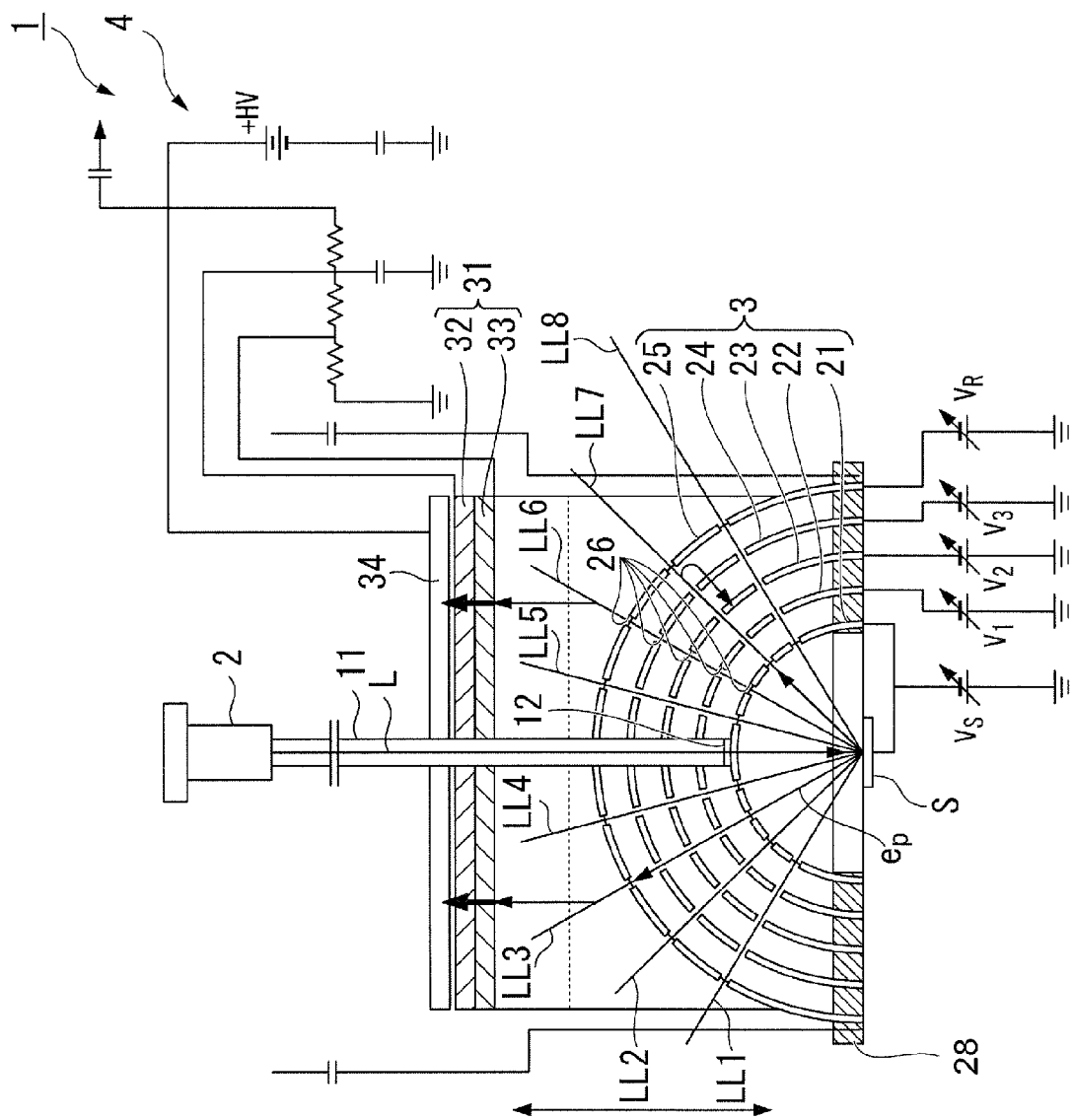
FIG. 1 is a cross-sectional view illustrating a photoelectron energy analyzer in accordance with a preferred embodiment of the present invention.
Figure 2:
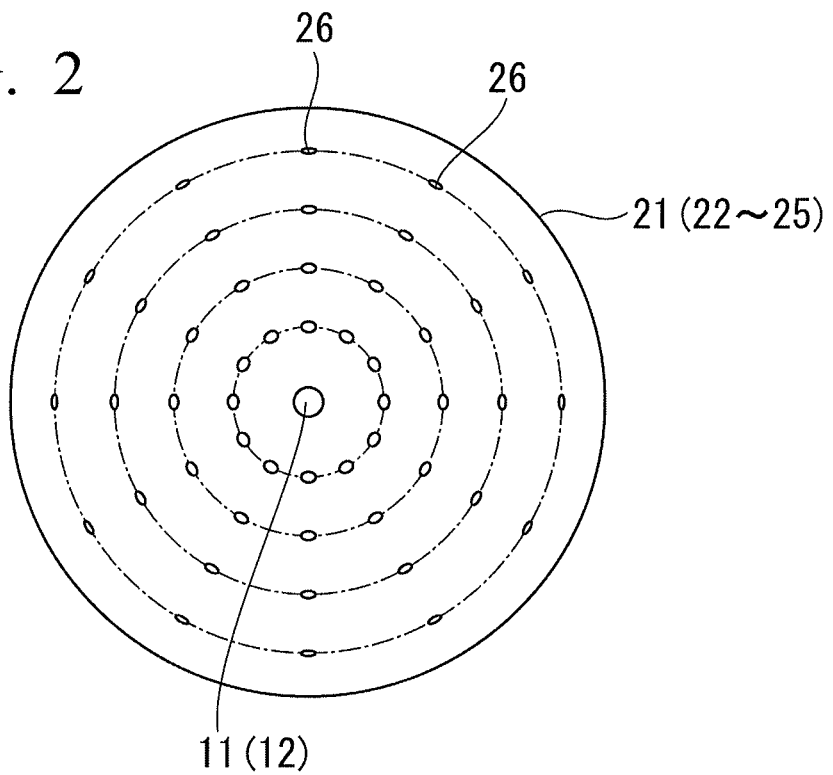
FIG. 2 is a plan view illustrating a spherical electrode part of the photoelectron energy analyzer in accordance with a preferred embodiment of the present invention.

FIG. 1 is a cross-sectional view illustrating a photoelectron energy analyzer in accordance with a preferred embodiment of the present invention. FIG. 2 is a plan view illustrating a spherical electrode part of the photoelectron energy analyzer in accordance with a preferred embodiment of the present invention. A photoelectron energy analyzer 1 includes a light source 2 configured to irradiate light L to a sample S, an electrode (member) 3 through which photoelectrons $e_p$ excited by the light L and emitted from the sample S pass, and a detector 4 configured to count and measure the photoelectrons $e_p$.

Here, the light source 2 may be a light source that can cause photoelectric emission of electrons from the sample S as photoelectrons by irradiation of the light L, for example, a rare gas discharge tube configured to emit ultraviolet light using a rare gas such as xenon (Xe). As other light sources, for example, a laser light source, a synchrotron radiation light source, a light emitting diode, and so on can be used.

A capillary tube (a guide part) 11 configured to guide the light L irradiated from the light source 2 to the sample S is mounted on the light source 2 such that the light L passing through the capillary tube 11 is focused and irradiated to the sample S through an optical lens 12.

An electrode 3 is constituted by a plurality of (five in FIG. 1) spherical electrode parts 21 to 25 formed of hemispherical conductive curved plates in which gold films are coated on oxygen-free copper, copper or a copper alloy, stainless steel, graphite, amorphous carbon, and so on, and the spherical electrode parts 21 to 25 are disposed at predetermined intervals from one another such that spherical center points of the spherical electrode parts 21 to 25 coincide with one another on a surface of the sample S.

Photoelectron passage openings 26 configured to extract photoelectrons $e_p$ from the sample S to the outside of the electrode 3 in a straight line are formed at positions of the spherical electrode parts 21 to 25 crossing a plurality of straight lines LL1 to LLn (n is an integer of 2 or more) radially extending from a surface of the sample. That is, as shown in FIGS. 1 and 2, the plurality of openings 26 are formed at predetermined intervals on four concentric circles about a central axis with respect to the spherical electrode parts 21 to 25.

In addition, in FIG. 1, the openings 26 are formed on eight straight lines LL1 to LL8 on a cross-section including a central axis, among the plurality of straight lines LL1 to LLn radially extending from the spherical electrode parts 21 to 25.

While shapes, sizes and density of the openings 26 (the number of openings per unit area on the spherical surface of the spherical electrode parts 21 to 25) may be of sufficient shapes, sizes and density to pass the photoelectrons $e_p$ therethrough, these are not limited thereto, but may have a circular shape that can form an electrostatic lens in cylindrical symmetry to detect the photoelectrons $e_p$ with high energy resolution.

Figure 3:
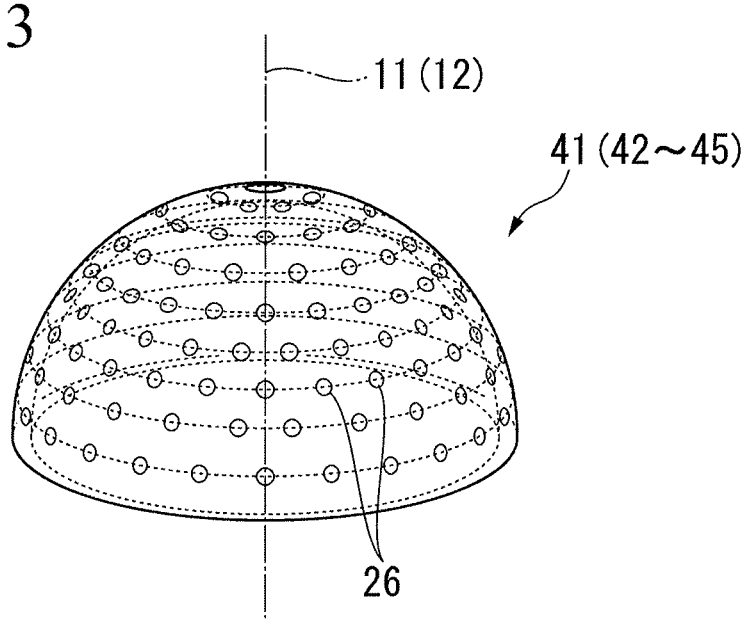
FIG. 3 is a perspective view illustrating a variant of the spherical electrode parts of the photoelectron energy analyzer in accordance with a preferred embodiment of the present invention.

FIG. 3 is a perspective view illustrating a variant of the spherical electrode parts 21 to 25 of the photoelectron energy analyzer in accordance with a preferred embodiment of the present invention. Spherical electrode parts 41 to 45 are distinguished from the spherical electrode parts 21 to 25 in which the openings 26 are formed at predetermined intervals on eight concentric circles about a central axis of the spherical electrode parts. The other parts are the same as the spherical electrode parts 21 to 25.

Figure 4:
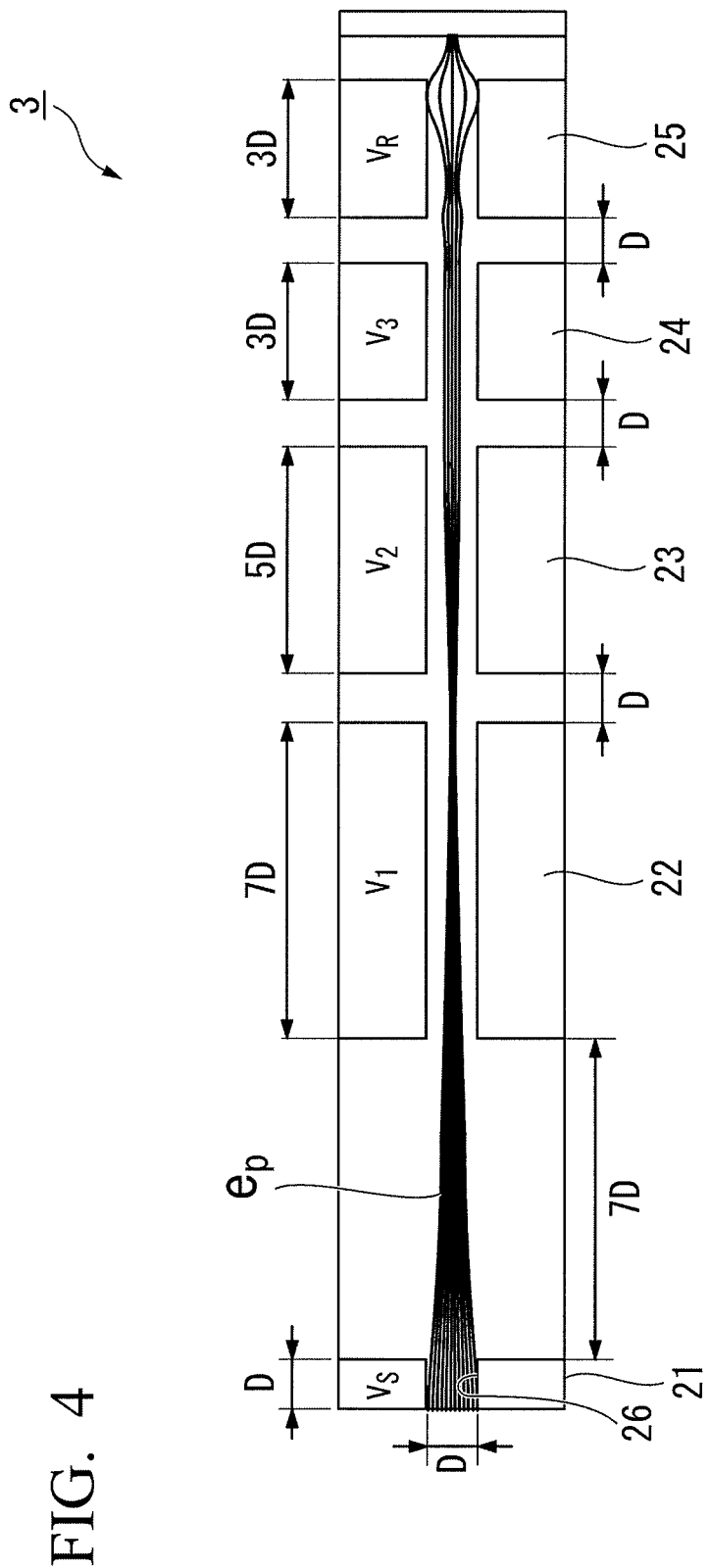
FIG. 4 is a partial cross-sectional view illustrating the spherical electrode parts of the photoelectron energy analyzer in accordance with a preferred embodiment of the present invention.

FIG. 4 is a partial cross-sectional view illustrating an example of a thickness of each of the plurality of spherical electrode parts 21 to 25 of the photoelectron energy analyzer and an interval between the plurality of spherical electrode parts 21 to 25 in accordance with a preferred embodiment of the present invention. An example of a thickness of each of the spherical electrode parts 21 to 25 and an interval between the spherical electrode parts 21 to 25 when the openings 26 have a diameter of D is shown.

In the electrode 3, a voltage Vs is applied to the innermost spherical electrode part 21 of the spherical electrode parts 21 to 25 to be the same potential as the sample S producing a space with no electric field between the spherical electrode part 21 and the sample S. In addition, voltages $V_1$, $V_2$ and $V_3$ are applied to the spherical electrode parts 22 to 24, respectively, and a trajectory of the photoelectrons $e_p$ can converge in a radial direction thereof by controlling the voltages $V_1$, $V_2$ and $V_3$. Further, a retarding voltage $V_R$ is applied to the outermost spherical electrode part 25 to form a retarding potential for selecting energy of the photoelectrons $e_p$ that have passed through the opening 26 of the spherical electrode part 24.

In the electrode 3, specific voltages are applied to the spherical electrode parts 21 to 25, respectively, and the electrode 3 functions as an assembly of electrostatic lenses that can make trajectories of the photoelectrons $e_p$ converge between the spherical electrode parts 21 to 25.

In addition, heating devices 28 are provided to the spherical electrode parts 21 to 25 to uniformly maintain shapes and work functions thereof, and thus, the spherical electrode parts 21 to 25 are maintained at a certain temperature using the heating devices 28, respectively, so that variation in work functions of the spherical electrode parts 21 to 25 is suppressed as much as possible, ultimately reducing the influence of work function change on energy resolution.

In addition, heating devices are additionally provided to the spherical electrode parts 21 to 25 to uniformly maintain shapes and work functions thereof, and thus, the spherical electrode parts 21 to 25 are maintained at a certain temperature using the heating devices, respectively, so that variation in work functions of the spherical electrode parts 21 to 25 is suppressed as much as possible, ultimately reducing the influence of work function change on energy resolution.

The detector 4 is an apparatus for counting and measuring the photoelectrons $e_p$ passing through the retarding electrode of the electrode 3, and a micro channel plate (MCP) 31 is a Chevron type, i.e., constituted by two overlapping plates 32 and 33, amplifying one electron to about $10^7$ times. The amplified electron can enter an anode 34 to be stored in a capacitor and is processed as a voltage signal.

In addition, the detector 4 can process a signal at each channel position of the MCP by using an MCP assembly capable of position detection, which consists of two-dimensionally divided anodes.

Next, a method of measuring a surface temperature of the sample S using the photoelectron energy analyzer 1 will be described.

Light L in a vacuum ultraviolet region emitted from the light source 2 is guided by the capillary tube 11 to be focused and irradiated to the surface of the sample S by the optical lens 12. In the sample S, electrons are excited by the irradiated light L and photoelectrons are emitted from the sample S. Here, emission of the electrons from the sample S depends on the excited electron energy and an escapable depth of the electrons is several atomic layers of the surface when the electrons are excited by the light L in the vacuum ultraviolet region. Accordingly, information on the electrons restricted to the several atomic layers of the surface is obtained. The electrons emitted from the surface have kinetic energy of an energy amount, in which a work function, i.e., energy corresponding to an electron potential difference between the inside of a solid material and a vacuum state, is subtracted from excitation energy by light.

Since the sample S and the spherical electrode part 21 have the same electric potential, there is no electric field affecting a flight trajectory of the electrons between the sample S and the spherical electrode part 21, and the photoelectrons $e_p$ radially emitted from the surface of the sample S freely fly toward the spherical electrode part 21 in a straight line.

While the photoelectrons $e_p$ arriving at the spherical electrode part 21 pass through the openings 26 of the spherical electrode parts 21 to 25, respectively, upon passing therethrough, the photoelectrons radially converge by the electrostatic lens effect by the voltages $V_1$ to $V_3$ applied to the spherical electrode parts 22 to 24, respectively, perpendicularly entering a center portion of the opening 26 of the spherical electrode part 25.

In order to refine the energy resolution, all of the photoelectrons $e_p$ passing through the opening 26 of the spherical electrode part 25 should pass over an equivalent potential formed by the retarding potential. For this, the photoelectrons $e_p$ should converge at the center portion of the opening 26 so that the photoelectrons $e_p$ perpendicularly enter the opening 26.

Here, only the photoelectrons $e_p$ having kinetic energy larger than the retarding potential among the photoelectrons $e_p$ perpendicularly entering the opening 26 of the spherical electrode part 25 pass through the opening 26, and the photoelectrons $e_p$ having kinetic energy smaller than the retarding potential cannot pass through the opening 26. Accordingly, as the retarding voltage $V_R$ is applied to the spherical electrode part 25, it is possible to select only the photoelectrons $e_p$ having kinetic energy larger than the retarding potential to pass through the opening 26.

The photoelectrons $e_p$ passing through the opening 26 of the spherical electrode part 25 are accelerated by the positive voltage applied to a front surface of the plate 33 of the MCP 31 to enter the plate 33.

The electrons are accelerated and amplified by a high voltage applied between the front surface of the plate 33 and a rear surface of the plate 32 to arrive at the anode 34. Electrical charges carried by the electrons of the anode 34 are converted into a voltage signal by the capacitor, and then, the voltage signal is counted and measured.

As the retarding potential is scanned, i.e., the voltage $V_R$ applied to the spherical electrode part 25 is scanned, and the voltages $V_1$, $V_2$ and $V_3$ respectively applied to the spherical electrode parts 22, 23 and 24 are appropriately controlled, it is possible to measure an integral spectrum, in which a horizontal axis represents $eV_R$ and a vertical axis represents a sum of electrons that can pass through the retarding potential. As the integral spectrum is differentiated by a computer, for example, an electron energy spectrum in which a horizontal axis represents electron energy and a vertical axis represents photoelectron intensity can be obtained. With respect to the electron energy spectrum, the Fermi distribution function is fitting-calculated using a temperature as a parameter, determining an absolute temperature T of the surface of the sample S.

Figure 5:
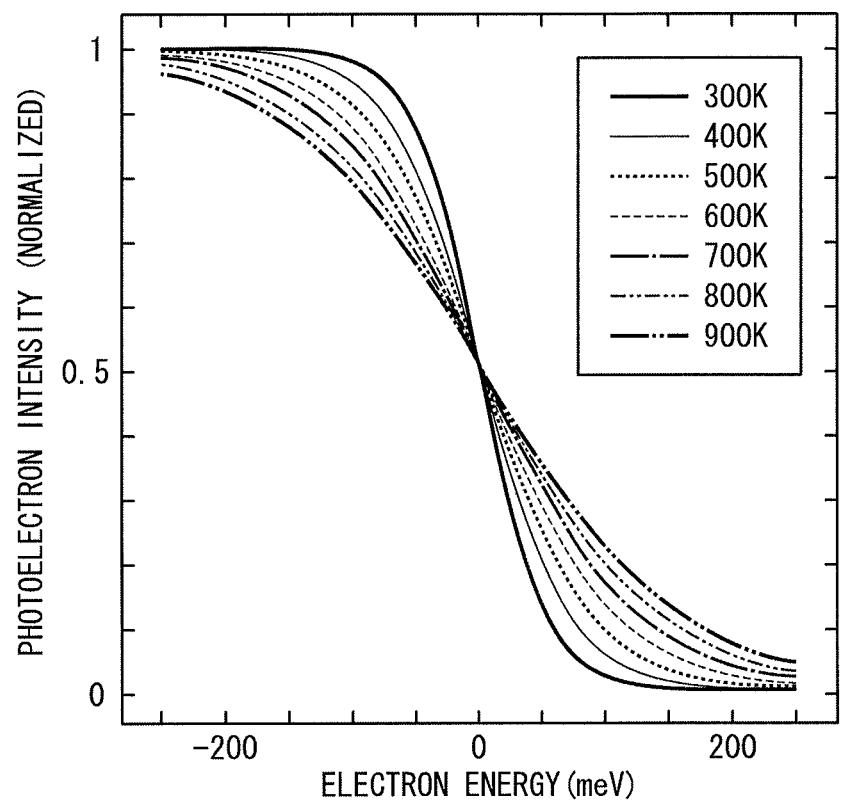
FIG. 5 is a diagram illustrating temperature dependency of a Fermi distribution function of a photoelectron.

FIG. 5 is a diagram illustrating temperature dependency of a Fermi distribution function of a photoelectron. Here, data are plotted with absolute temperatures from 300K to 900K at intervals of 100K.

As described above, since the Fermi distribution function of the photoelectron may be unambiguously determined by the absolute temperature T, the Fermi distribution function of equation (1) is fitted to the electron energy spectrum obtained from the integral photoelectron spectrum by differentiating, determining the surface temperature of the sample S with high resolution.

The most important characteristic of the photoelectron energy analyzer 1 is that the photoelectron energy analyzer 1 possesses an electrostatic lens system that can make trajectories of the photoelectrons $e_p$ converge between the spherical electrode parts 21 to 25 by applying the voltages to the respective spherical electrode parts 21 to 25.

Since a hemispherical retarding electrode used, for example, in a conventional low electron energy diffraction (LEED) apparatus or a conventional Auger electron spectrometer is formed of a metal mesh, electrons move in the electrostatic potential made by the metal mesh. In this case, since the electrostatic potential of the metal mesh surface is microscopically non-uniform and a straight flight trajectory of the electrons is deflected due to a Coulomb's force working between a metal wire constituting the metal mesh and the electron, kinetic energy of the electrons that can be measured by the method is about 100 eV, and energy resolution is limited to 0.1 eV, which is 0.1% of 100 eV.

Meanwhile, in the photoelectron energy analyzer 1 of the embodiment specific voltages are applied to the spherical electrode parts 21 to 25, respectively, to perform a function of the electrostatic lens system that can make the trajectories of the photoelectrons $e_p$ converge between the spherical electrode parts 21 to 25. In addition, since the retarding voltage $V_R$ is applied to the spherical electrode part 25 to select energy of the photoelectrons $e_p$, the photoelectrons $e_p$ emitted in a hemispherical direction can be detected at a wide solid angle. Accordingly, the photoelectrons $e_p$ can be detected with high energy resolution of about 1 meV and high sensitivity.

Further, when the MCP assembly capable of position detection, which includes two-dimensionally arrayed anodes, is used for the detection unit 4, counting and measurement of the electrons at each emission angle of the electrons emitted from the sample can be performed. Accordingly, an angle-resolved photoelectron spectrum can be measured at a high speed within a wide range of the emission angle of the electrons emitted from the sample surface.

Here, a computer simulated result of the energy resolution of the photoelectron spectrum with the photoelectron energy analyzer will be described.

The spherical electrode parts were disposed in an arrangement shown in FIG. 3. Gold having a work function of 5.4 eV was assumed as a sample and a Xe gas discharge lamp having photon energy of 9.6 eV was assumed as a light source. In this case, the photoelectrons emitted from the Fermi energy had kinetic energy of 4.2 eV.

In addition, a voltage $V_s$ of the spherical electrode part 21 was 0 V, a voltage $V_1$ of the spherical electrode part 22 was +10.000 V, a voltage $V_2$ of the spherical electrode part 23 was +1.000 V, a voltage $V_3$ of the spherical electrode part 24 was −4.100 V, and a voltage $V_R$ of the spherical electrode part 25 was −4.200 V. Table 1 shows calculated results. In Table 1, r represents a radius of the opening of the spherical electrode part 21, and 2r=D.

TABLE 1

| Ek(eV) | 0 | ±0.1 r | ±0.2 r | ±0.3 r | ±0.4 r | ±0.5 r | ±0.6 r | ±0.7 r | ±0.8 r | ±0.9 r |
|---|---|---|---|---|---|---|---|---|---|---|
| 4.195 | x | x | x | x | x | x | x | x | x | x |
| 4.196 | x | x | x | x | x | x | x | x | x | x |
| 4.197 | x | x | x | x | x | x | x | x | x | x |

TABLE 1-continued

| Ek(eV) | 0 | ±0.1 r | ±0.2 r | ±0.3 r | ±0.4 r | ±0.5 r | ±0.6 r | ±0.7 r | ±0.8 r | ±0.9 r |
|---|---|---|---|---|---|---|---|---|---|---|
| 4.198 | x | x | x | x | x | x | x | x | x | x |
| 4.199 | x | x | x | x | x | x | x | x | x | x |
| 4.200 | x | x | x | x | x | x | x | x | x | x |
| 4.201 | x | ○ | ○ | ○ | ○ | x | ○ | ○ | x | x |
| 4.202 | ○ | ○ | ○ | ○ | ○ | ○ | ○ | ○ | ○ | x |
| 4.203 | ○ | ○ | ○ | ○ | ○ | ○ | ○ | ○ | ○ | ○ |
| 4.204 | ○ | ○ | ○ | ○ | ○ | ○ | ○ | ○ | ○ | ○ |
| 4.205 | ○ | ○ | ○ | ○ | ○ | ○ | ○ | ○ | ○ | ○ |
| 4.206 | ○ | ○ | ○ | ○ | ○ | ○ | ○ | ○ | ○ | ○ |

Here, provided that the kinetic energy of the electrons photo-electrically emitted from around the Fermi energy level perpendicularly passes through the opening of the spherical electrode part 21, 19 electrons passing through the opening (an opening center position is set as 0, and the electrons were distributed from the opening center position to −0.9r to +0.9r at intervals of 0.1r) pass through the spherical electrode part 21 with a kinetic energy of 4.195 to 4.206. In Table 1 and in all of the Tables following, the case in which the electrons passed the spherical electrode part 25 is represented as "○," and the case in which the electrons did not pass the spherical electrode part 25 is represented as "x."

According to the calculated results, from the fact that the electrons of 4.200 eV or less cannot pass and the electrons of 4.203 eV or more can pass, it will be appreciated that uncertainty of success and failure of passage of the electrons is within a range of 4.2015±0.001 eV and the energy resolution is about 1 meV.

Results of the same computer simulation performed with respect to the photoelectrons having energy higher than the Fermi energy level by 200 meV (+200 meV) are represented in Table 4, and results of the same computer simulation performed with respect to the photoelectrons having energy lower than the Fermi energy level by 200 meV (−200 meV) are represented in Table 5.

TABLE 2

| Ek(eV) | 0 | ±0.1 r | ±0.2 r | ±0.3 r | ±0.4 r | ±0.5 r | ±0.6 r | ±0.7 r | ±0.8 r | ±0.9 r |
|---|---|---|---|---|---|---|---|---|---|---|
| 4.295 | x | x | x | x | x | x | x | x | x | x |
| 4.296 | x | x | x | x | x | x | x | x | x | x |
| 4.297 | x | x | x | x | x | x | x | x | x | x |
| 4.298 | x | x | x | x | x | x | x | x | x | x |
| 4.299 | x | x | x | x | x | x | x | x | x | x |
| 4.300 | x | x | x | x | x | x | x | x | x | x |
| 4.301 | x | ○ | ○ | ○ | ○ | x | ○ | ○ | x | x |
| 4.302 | ○ | ○ | ○ | ○ | ○ | ○ | ○ | ○ | ○ | x |
| 4.303 | ○ | ○ | ○ | ○ | ○ | ○ | ○ | ○ | ○ | ○ |
| 4.304 | ○ | ○ | ○ | ○ | ○ | ○ | ○ | ○ | ○ | ○ |
| 4.305 | ○ | ○ | ○ | ○ | ○ | ○ | ○ | ○ | ○ | ○ |
| 4.306 | ○ | ○ | ○ | ○ | ○ | ○ | ○ | ○ | ○ | ○ |

TABLE 3

| Ek(eV) | 0 | ±0.1 r | ±0.2 r | ±0.3 r | ±0.4 r | ±0.5 r | ±0.6 r | ±0.7 r | ±0.8 r | ±0.9 r |
|---|---|---|---|---|---|---|---|---|---|---|
| 4.095 | x | x | x | x | x | x | x | x | x | x |
| 4.096 | x | x | x | x | x | x | x | x | x | x |
| 4.097 | x | x | x | x | x | x | x | x | x | x |
| 4.098 | x | x | x | x | x | x | x | x | x | x |
| 4.099 | x | x | x | x | x | x | x | x | x | x |
| 4.100 | x | x | x | x | x | x | x | x | x | x |
| 4.101 | x | ○ | ○ | ○ | ○ | x | ○ | ○ | x | x |
| 4.102 | ○ | ○ | ○ | ○ | ○ | ○ | ○ | ○ | ○ | x |
| 4.103 | ○ | ○ | ○ | ○ | ○ | ○ | ○ | ○ | ○ | ○ |
| 4.104 | ○ | ○ | ○ | ○ | ○ | ○ | ○ | ○ | ○ | ○ |
| 4.105 | ○ | ○ | ○ | ○ | ○ | ○ | ○ | ○ | ○ | ○ |
| 4.106 | ○ | ○ | ○ | ○ | ○ | ○ | ○ | ○ | ○ | ○ |

Here, with respect to the electron energy of +100 meV, i.e., the kinetic energy of about 4.3 eV, a voltage $V_1$ of the spherical electrode part 22 was +10.238 V, a voltage $V_2$ of the spherical electrode part 23 was +1.024 V, a voltage $V_3$ of the spherical electrode part 24 was −4.198 V, and a voltage $V_R$ of the spherical electrode part 25 was −4.300 V.

In addition, with respect to the electron energy of −100 meV, i.e., the kinetic energy of about 4.1 eV, a voltage $V_1$ of the spherical electrode part 22 was +9.762 V, a voltage $V_2$ of the spherical electrode part 23 was +0.976 V, a voltage $V_3$ of the spherical electrode part 24 was −4.002 V, and a voltage $V_R$ of the spherical electrode part 25 was −4.100 V.

According to the calculated results, with respect to the case of +100 meV, it will be appreciated that uncertainty of success and failure of passage of the electrons is within a range of 4.3015±0.001 eV and the energy resolution is about 1 meV.

In addition, with respect to the case of −100 meV, it will be appreciated that uncertainty of success and failure of passage of the electrons is within a range of 4.1015±0.001 eV and the energy resolution is about 1 meV.

Results of the same calculator simulation performed with respect to the photoelectrons having energy higher than the Fermi energy level by 200 meV (+200 meV) are represented in Table 4, and results of the same computer simulation performed with respect to the photoelectrons having energy lower than the Fermi energy level by 200 meV (−200 meV) are represented in Table 5.

the spherical electrode part 23 was +0.952 V, a voltage $V_3$ of the spherical electrode part 24 was −3.905 V, and a voltage $V_R$ of the spherical electrode part 25 was −4.000 V.

According to the calculated results, with respect to the case of +200 meV, it will be appreciated that uncertainty of success and failure of passage of the electrons is within a range of 4.4015±0.001 eV and the energy resolution is about 1 meV.

In addition, with respect to the case of −200 meV, it will be appreciated that uncertainty of success and failure of passage of the electrons is within a range of 4.00150.001 eV and the energy resolution is about 1 meV.

According to the computer simulation results of the energy resolution of the photoelectrons $e_p$, with respect to the photoelectrons having a range of ±200 meV of the Fermi energy level, it will be appreciated that effective energy resolution of about 1 meV can be obtained.

Figure 6:
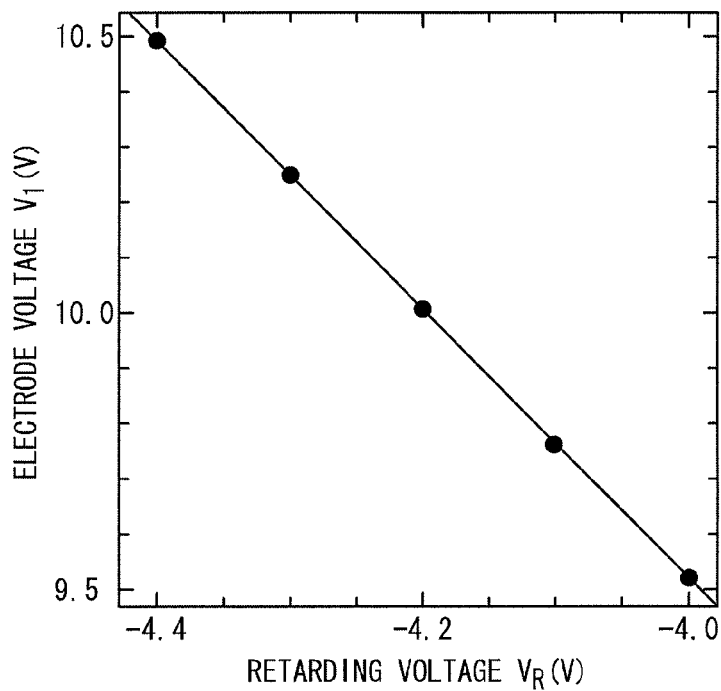
FIG. 6 is a diagram illustrating a relationship between the voltage $V_1$ of the spherical electrode part 22 and the retarding voltage $V_R$ in the computer simulation.
Figure 7:
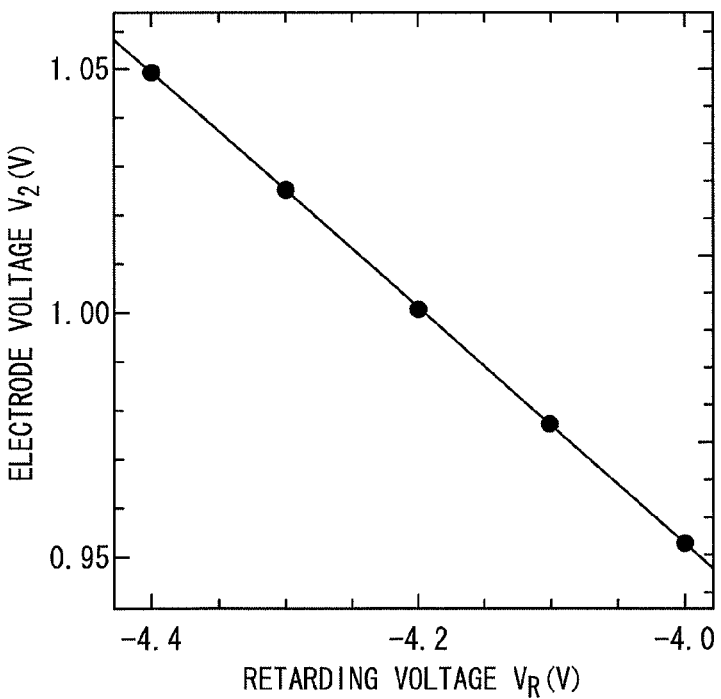
FIG. 7 is a diagram illustrating a relationship between the voltage $V_2$ of the spherical electrode part 23 and the retarding voltage $V_R$ in the computer simulation.
Figure 8:
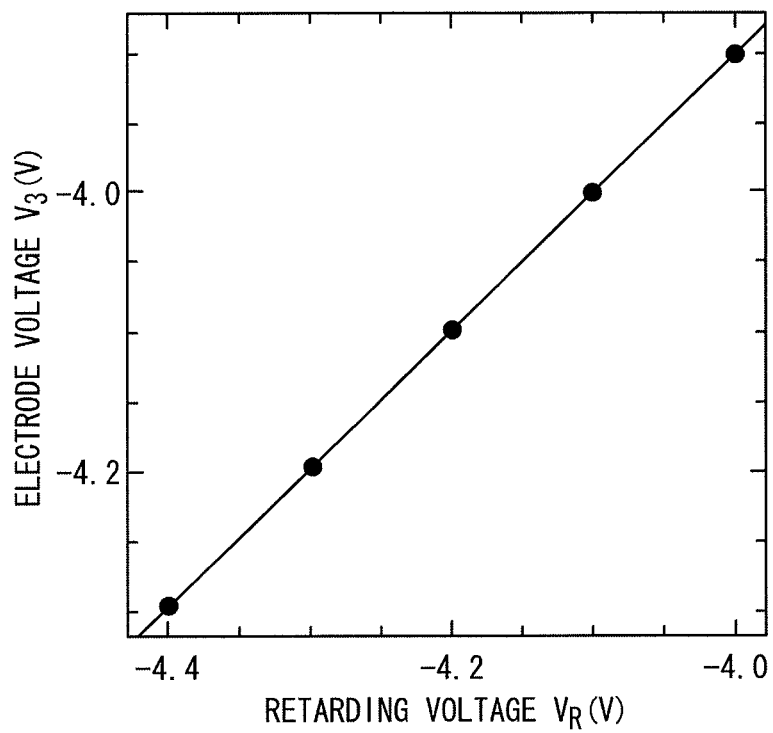
FIG. 8 is a diagram illustrating a relationship between the voltage $V_3$ of the spherical electrode part 24 and the retarding voltage $V_R$ in the computer simulation.

FIG. 6 is a diagram illustrating a relationship between the voltage $V_1$ of the spherical electrode part 22 and the retarding voltage $V_R$ in the computer simulation. FIG. 7 is a diagram illustrating a relationship between the voltage $V_2$ of the spherical electrode part 23 and the retarding voltage $V_R$ in the computer simulation. FIG. 8 is a diagram illustrating a relationship between the voltage $V_3$ of the spherical electrode part 24 and the retarding voltage $V_R$ in the computer simulation.

Referring to FIGS. 6 to 8, it will be appreciated that all of the voltages $V_1$, $V_2$ and $V_3$ are in proportion to the retarding voltage $V_R$ applied to the spherical electrode part 25. This

TABLE 4

| Ek(eV) | 0 | ±0.1 r | ±0.2 r | ±0.3 r | ±0.4 r | ±0.5 r | ±0.6 r | ±0.7 r | ±0.8 r | ±0.9 r |
|---|---|---|---|---|---|---|---|---|---|---|
| 4.395 | x | x | x | x | x | x | x | x | x | x |
| 4.396 | x | x | x | x | x | x | x | x | x | x |
| 4.397 | x | x | x | x | x | x | x | x | x | x |
| 4.398 | x | x | x | x | x | x | x | x | x | x |
| 4.399 | x | x | x | x | x | x | x | x | x | x |
| 4.400 | x | x | x | x | x | x | x | x | x | x |
| 4.401 | x | o | o | o | o | x | o | o | x | x |
| 4.402 | o | o | o | o | o | o | o | o | o | x |
| 4.403 | o | o | o | o | o | o | o | o | o | o |
| 4.404 | o | o | o | o | o | o | o | o | o | o |
| 4.405 | o | o | o | o | o | o | o | o | o | o |
| 4.406 | o | o | o | o | o | o | o | o | o | o |

TABLE 5

| Ek(eV) | 0 | ±0.1 r | ±0.2 r | ±0.3 r | ±0.4 r | ±0.5 r | ±0.6 r | ±0.7 r | ±0.8 r | ±0.9 r |
|---|---|---|---|---|---|---|---|---|---|---|
| 3.995 | x | x | x | x | x | x | x | x | x | x |
| 3.996 | x | x | x | x | x | x | x | x | x | x |
| 3.997 | x | x | x | x | x | x | x | x | x | x |
| 3.998 | x | x | x | x | x | x | x | x | x | x |
| 3.999 | x | x | x | x | x | x | x | x | x | x |
| 4.000 | x | x | x | x | x | x | x | o | x | x |
| 4.001 | x | o | o | o | o | x | o | o | x | x |
| 4.002 | o | o | o | o | o | o | o | o | o | o |
| 4.003 | o | o | o | o | o | o | o | o | o | o |
| 4.004 | o | o | o | o | o | o | o | o | o | o |
| 4.005 | o | o | o | o | o | o | o | o | o | o |
| 4.006 | o | o | o | o | o | o | o | o | o | o |

Here, with respect to the electron energy of +200 meV, i.e., the kinetic energy of about 4.4 eV, a voltage $V_1$ of the spherical electrode part 22 was +10.476 V, a voltage $V_2$ of the spherical electrode part 23 was +1.048 V, a voltage $V_3$ of the spherical electrode part 24 was −4.295 V, and a voltage $V_R$ of the spherical electrode part 25 was −4.400 V.

In addition, with respect to the electron energy of −200 meV, i.e., the kinetic energy of about 4.0 eV, a voltage $V_1$ of the spherical electrode part 22 was +9.524 V, a voltage $V_2$ of means that electrode voltages required upon measurement of photoelectron spectrum can be easily controlled.

While the sample is assumed as gold in the above computer simulation, another sample excepting gold has a different work function. Accordingly, when the Xe gas discharge lamp is used as a light source, the photoelectrons excited around the Fermi energy level have a kinetic energy different from 4.2 eV. Even in this case, when the computer simulation of the kinetic energy of the photoelectrons excited around the Fermi energy level is performed, the same energy resolution can be obtained.

According to the photoelectron energy analyzer 1 of the embodiment, the specific voltages are applied to the spherical electrode parts 21 to 25, respectively, to perform a function of an electrostatic lens system that can make a trajectory of the photoelectrons $e_p$ converge between the spherical electrode parts 21 to 25. In addition, since the retarding voltage $V_R$ is applied to the spherical electrode part 25 to select energy of the photoelectrons $e_p$, all of the photoelectrons $e_p$ emitted in a hemispherical direction can be detected and the energy of the photoelectrons $e_p$ can be measured with a high resolution of about 1 meV.

Further, since the plurality of photoelectron passage openings are formed at the spherical electrode parts 21 to 25, respectively, a very simple and compact configuration can be implemented.

Furthermore, as the photoelectron energy analyzer 1 of the embodiment is mounted on a surface analysis apparatus such as a scanning electron microscope (SEM) or an X-ray photoelectron spectrometer (XPS), a material research apparatus, a surface reaction control apparatus, and so on, simultaneous and multi-functional measurement including surface temperature measurement can be performed to improve multi-functionality, high functionality and reliability of these apparatuses.

In addition, since the photoelectron energy analyzer 1 of the present embodiment is a thermometer for absolute temperature measurement that does not require calibration using, for example, a temperature fixed point, and a measurement region is specified within several atomic layers, a use as a novel standard thermometer (surface temperature) in a measurement standard field may be anticipated.

While preferred embodiments of the invention have been described and illustrated above, it should be understood that these are exemplary of the invention and are not to be considered as limiting. Additions, omissions, substitutions, and other modifications can be made without departing from the scope of the present invention.

INDUSTRIAL APPLICABILITY

The photoelectron energy analyzer of the present invention includes the electrode configured to detect and count electrons. The electrode includes the plurality of spherical electrode parts having different radii of spherical parts. The spherical electrode parts are disposed in an insulated state such that spherical center points thereof are overlapped to coincide with an electron emission position and voltages are independently applied to the spherical electrode parts. The electron passage openings, through which the electrons can be perpendicularly extracted to the outside of the electrode, are formed at positions of the spherical electrode parts crossing a plurality of straight lines radially extending from the spherical center point. Accordingly, high sensitivity measurement can be performed with high energy resolution. As a result, an absolute temperature (thermodynamic temperature) on a surface of a metal can be measured with high precision, and a use as a standard surface temperature thermometer may be possible. In addition, for example, applications to non-contact temperature measurement under ultrahigh vacuum environments, a high sensitivity and high energy resolution electron energy analyzer in various surface analysis apparatuses, or a high speed angular-resolved photoelectron spectroscopic measurement apparatus for physical property research are also effective, and their industrial and scientific values are very high.

The invention claimed is:

1. An electrode member comprising:
a plurality of concentric spherical electrode parts having a spherical center point, each of the plurality of concentric spherical electrode parts having a radius, each of the plurality of spherical electrode parts being formed by a spherical plate, the radii being different from each other, and
heating devices provided for the plurality of concentric spherical electrode parts, wherein
each of the plurality of concentric spherical electrode parts are disposed in an insulated state and voltages are independently applied to each of the plurality of concentric spherical electrode parts,
electron passage openings are configured to extract electrons moving from the spherical center point to an outside of each spherical electrode part, the electron passage openings being respectively formed at positions on each of the plurality of concentric spherical electrode parts crossing a plurality of straight lines radially extending from the spherical center point, and
voltages are applied to each of the plurality of concentric spherical electrode parts, respectively, so that the electron passage openings function as electrostatic lenses that cause a trajectory of electrons passing through each of the electron passage openings to converge around a center of the opening.

2. An electron energy analyzer having the electrode member according to claim 1.

3. A photoelectron energy analyzer having the electron energy analyzer according to claim 2, further comprising:
an excitation light source configured to irradiate a sample to cause the sample to emit photoelectrons from a surface of the sample disposed so as to include the spherical center point of the plurality of concentric spherical electrode parts, and
an electron detector part configured to detect the photoelectrons emitted from the surface of the sample disposed so as to include the spherical center point.

4. The photoelectron energy analyzer according to claim 3, wherein the excitation light source has a guide part configured to guide light irradiated from the excitation light source to the spherical center point of the plurality of concentric spherical electrode parts.

5. A temperature measuring apparatus having a photoelectron energy analyzer, the photoelectron energy analyzer having an electron energy analyzer, the electron energy analyzer having an electrode member comprising:
a plurality of concentric spherical electrode parts having a spherical center point, each of the plurality of concentric spherical electrode parts having a radius, each of the plurality of spherical electrode parts being formed by a spherical plate, the radii being different from each other,
an excitation light source configured to irradiate a sample to cause the sample to emit photoelectrons from a surface of the sample disposed so as to include the spherical center point of the plurality of concentric spherical electrode parts, and
an electron detector part configured to detect the photoelectrons emitted from the surface of the sample disposed so as to include the spherical center point, wherein each of the plurality of concentric spherical electrode parts are disposed in an insulated state and voltages are independently applied to each of the plurality of concentric spherical electrode parts, electron passage openings are configured to extract electrons moving from the spherical center point to an outside of each spherical electrode part, the electron passage openings being respectively formed at positions on each of the plurality of concentric spherical electrode parts crossing a plurality of straight lines radially extending from the spherical center point, and voltages are applied to each of the plurality of concentric spherical electrode parts, respectively, so that the electron passage openings function as electrostatic lenses that cause a trajectory of electrons passing through each of the electron passage openings to converge around a center of the opening.

6. A temperature measuring apparatus having a photoelectron energy analyzer, the photoelectron energy analyzer having an electron energy analyzer, the electron energy analyzer having an electrode member comprising:

a plurality of concentric spherical electrode parts having a spherical center point, each of the plurality of concentric spherical electrode parts having a radius, each of the plurality of spherical electrode parts being formed by a spherical plate, the radii being different from each other, an excitation light source configured to irradiate a sample to cause the sample to emit photoelectrons from a surface of the sample disposed so as to include the spherical center point of the plurality of concentric spherical electrode parts, and an electron detector part configured to detect the photoelectrons emitted from the surface of the sample disposed so as to include the spherical center point, wherein the excitation light source has a guide part configured to guide light irradiated from the excitation light source to the spherical center point of the plurality of concentric spherical electrode parts, each of the plurality of concentric spherical electrode parts are disposed in an insulated state and voltages are independently applied to each of the plurality of concentric spherical electrode parts, electron passage openings are configured to extract electrons moving from the spherical center point to an outside of each spherical electrode part, the electron passage openings being respectively formed at positions on each of the plurality of concentric spherical electrode parts crossing a plurality of straight lines radially extending from the spherical center point, and voltages are applied to each of the plurality of concentric spherical electrode parts, respectively, so that the electron passage openings function as electrostatic lenses that cause a trajectory of electrons passing through each of the electron passage openings to converge around a center of the opening.

* * * * *